United States Patent
Walter et al.

(10) Patent No.: US 8,192,136 B2
(45) Date of Patent: Jun. 5, 2012

(54) APPARATUS AND METHOD FOR STORING AT LEAST ONE SPECIMEN SLIDE AND AT LEAST ONE CASSETTE

(75) Inventors: Roland Walter, Reilingen (DE); Christoph Schmitt, Schriesheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 351 days.

(21) Appl. No.: 12/567,440

(22) Filed: Sep. 25, 2009

(65) Prior Publication Data

US 2010/0083777 A1 Apr. 8, 2010

(30) Foreign Application Priority Data

Oct. 6, 2008 (DE) .......................... 10 2008 050 530

(51) Int. Cl.
*B01L 9/00* (2006.01)
*B01L 9/06* (2006.01)
*B65D 21/02* (2006.01)

(52) U.S. Cl. .................. 414/800; 73/864.91; 220/23.4; 220/232; 220/507; 206/232; 206/443; 206/557; 206/561

(58) Field of Classification Search .................. 206/456; 220/23.4, 23.8, 345.1, 4.26, 4.27, 820; 359/393; 414/800; 83/167, 170, 915.5
See application file for complete search history.

(56) References Cited

U.S. PATENT DOCUMENTS

| | | | | |
|---|---|---|---|---|
| 2,407,021 A * | 9/1946 | Langel | ......................... | 220/23.4 |
| 2,998,665 A | 9/1961 | Diemer | | |
| 3,131,826 A | 5/1964 | Wiklund | | |
| 3,603,474 A * | 9/1971 | Erickson | ...................... | 220/23.4 |
| 3,647,105 A * | 3/1972 | Keeslar | .......................... | 220/23.4 |
| 3,701,079 A * | 10/1972 | Bowden et al. | ............... | 439/892 |
| 4,328,902 A * | 5/1982 | North | ............................ | 220/23.4 |
| 4,802,601 A * | 2/1989 | Pijanowski et al. | .......... | 220/4.01 |
| 5,021,218 A * | 6/1991 | Davis et al. | ................... | 422/563 |
| 5,080,869 A * | 1/1992 | McCormick | .................. | 422/547 |
| 6,899,228 B2 * | 5/2005 | Kiene et al. | .................... | 206/456 |
| 2005/0112031 A1 | 5/2005 | McCormick | | |
| 2005/0235542 A1 | 10/2005 | Metzner et al. | | |
| 2007/0204734 A1* | 9/2007 | Ito et al. | .......................... | 83/170 |
| 2010/0083777 A1* | 4/2010 | Walter et al. | ............... | 73/864.91 |

FOREIGN PATENT DOCUMENTS

| | | |
|---|---|---|
| DE | 1117321 | 5/1960 |
| DE | 2636628 | 2/1978 |
| DE | 3148438 | 8/1982 |
| DE | 3210396 | 9/1983 |
| DE | 3325241 | 1/1985 |
| DE | 19742493 | 2/1999 |
| DE | 10154843 | 5/2003 |
| DE | 202004006265 | 7/2004 |
| DE | 202005017383 | 2/2006 |
| DE | 102007059392 | 10/2008 |
| GB | 1528315 | 10/1978 |

* cited by examiner

*Primary Examiner* — Gregory Adams
(74) *Attorney, Agent, or Firm* — Schlee IP International, P.C.; Alexander R. Schlee

(57) ABSTRACT

An apparatus for storing at least one specimen slide and at least one cassette comprising a sample that is embedded in a sample block and that is to be processed, a microtome comprising this apparatus, and a method for handling multiple cassettes and multiple specimen slides are described. A cassette magazine receives at least one cassette having at least one sample block. A slide magazine receives at least one specimen slide. At least one connecting element for connecting the cassette magazine and the slide magazine mechanically with each other is provided. This allows handling at least one cassette and at least one specimen slide together in a simple and efficient manner.

12 Claims, 4 Drawing Sheets

APPARATUS AND METHOD FOR STORING AT LEAST ONE SPECIMEN SLIDE AND AT LEAST ONE CASSETTE

CROSS-REFERENCE TO RELATED APPLICATION

This application claims the priority of the German patent application DE 102008050530.7 having a filing date of Oct. 6, 2008. The entire content of this prior German patent application DE 102008050530.7 is herewith incorporated by reference.

BACKGROUND OF THE INVENTION

The invention relates to an apparatus for storing at least one specimen slide and at least one cassette having a sample, embedded in a sample block, that is to be processed. The apparatus encompasses a cassette magazine in which is arranged at least one cassette having at least one sample block, and a slide magazine in which at least one specimen slide is arranged. The invention further relates to a method for handling multiple cassettes each having at least one sample block having a sample to be processed, and multiple specimen slides.

The apparatus and the method are preferably utilized in histological technology. Histological technology deals with the investigation of tissue samples from patients. The most common method is to embed in paraffin the tissue sample taken from the patient, cut thin sections from the resulting sample blocks using a microtome, mount each thin section onto a specimen slide, stain them in a further process, cover each with a coverslip, and deliver them to a microscope for diagnostic evaluation. Some or all of the individual steps just described are preferably executed automatically. A sample block is delivered to the microtome in a cassette, the sample block being fixedly joined to the cassette and the sample block being held in the microtome by way of the cassette.

It is necessary for the tissue samples to be uniquely identifiable continuously through all the process steps. The intention thereby is to preclude confusion among samples, in order to avoid incorrect allocation of a sample, a thin section, or an investigation result. An incorrect allocation can cause a healthy patient to be considered ill, and an ill patient to be erroneously considered healthy. Medical actions that might be necessary are then omitted or are instituted only after a delay. A further intention is to avoid sample loss. In order to achieve unique identifiability, all cassettes carry a unique identifier. The difficulty lies in also identifying with an identifier the specimen slides on which a thin section of a sample block has been mounted. The identifier on the specimen slide should be uniquely allocatable to the identifier of the cassette from which the sample block was taken. The identifier of the cassette and the identifier of the corresponding specimen slide are preferably identical. Three methods, which will be briefly explained below, can be used to identify the specimen slide.

In the first method, the specimen slides are labeled manually after the thin section has been mounted onto the specimen slide. This manual labeling of course entails considerable susceptibility to error due to confusion. Manual labeling is further problematic because the label must be read later by other persons, and a manual label is more susceptible to error when being read than a mechanical label.

A further possible method involves already labeling the specimen slide before it is delivered to the microtome and thus before the thin sections are mounted. Labeling can be performed manually or mechanically. Transport of the specimen slides to the microtome, and of the cassettes having the sample blocks to the microtome, occurs separately. It is disadvantageous that after a thin section is produced with the use of the microtome, the matching pre-labeled specimen slide must be located from among a plurality of specimen slides. This requires a manual comparison between the specimen slide identifier and the cassette identifier. This manual comparison and manual identification are associated with relatively high complexity.

In the third possible method, the cassettes having the sample blocks are conveyed in a cassette magazine to a microtome. During processing of a sample block, the identifier of the cassette belonging to it is read off. A labeling unit for labeling specimen slides is arranged next to the microtome. Labeling of a specimen slide occurs concurrently with production of a thin section in the microtome: the identifier on the specimen slide corresponds to the identifier read off from the cassette, or can be allocated to that identifier. Any confusion of specimen slides can thereby very largely be precluded, since labeling of the specimen slides takes place concurrently with production of the thin sections, and only that specimen slide is present in the apparatus. A disadvantage of this method is that a labeling unit for labeling specimen slides must be arranged in parallel with each microtome, which results in a considerable cost outlay when there are many microtomes. A large amount of space can also be required as a result.

The document DE 10154843 A1 discloses a method and an apparatus for identifying specimen slides for microtomed tissue samples and for the processing thereof, in which the identifier information pertinent to a slide is automatically sensed while said slide is arranged in the microtome, and an identifier allocated to that identifier is automatically transferred onto at least one specimen slide. At the point in time at which a microtomed tissue sample must be mounted onto a specimen slide, only that specimen slide equipped with the identifier is presented at the microtome workstation.

A magazine having compartments for the reception of cassettes is known from the previously unpublished document DE 10 2007 059392. The magazine has an external housing having an apparatus arranged therein for stepwise advancing of the cassettes from one compartment to the next compartment.

The document DE 20 2004 006265 discloses a microtome for producing thin sections, which encompasses a reading device for coded information applied onto the cassette. The apparatus further encompasses a control device having a computer for the coordination of all functional sequences. With the aid of the reading device, a code arranged on a magazine having compartments can be read out. The magazine serves to receive prepared cassettes. The microtome further encompasses a handling device for controllable removal of a cassette and for positioning on a sample receptacle of the microtome, and for return into the magazine. The reading device can be arranged in the magazine housing or in the handling device.

SUMMARY OF THE INVENTION

It is the object of the invention to describe an apparatus and a method in which, in simple fashion, at least one cassette and at least one specimen slide can be handled together.

This object is achieved in an apparatus for storing at least one specimen slide and at least one cassette comprising a sample that is embedded in a sample block and that is to be processed, said apparatus comprising: a cassette magazine adapted to receive at least one cassette having at least one sample block; a slide magazine adapted to receive at least one specimen slide; and at least one connecting element for connecting the cassette magazine and the slide magazine mechanically with each other. This object is achieved further by a microtome comprising said apparatus, and by a method for handling by means of said apparatus multiple cassettes that each have at least one sample block having a sample to be processed, and for handling multiple specimen slides.

What is achieved by means of an apparatus having the features of claim 1 is that a cassette magazine in which at least one cassette having at least one sample block is arrangeable, and a slide magazine in which at least one specimen slide is arrangeable, are connectable to one another in simple fashion with the aid of at least one connecting element, so that a simple and unique allocation is possible between the cassette magazine and the cassettes present therein, and the slide magazine and the specimen slides present therein.

It is advantageous that the cassette magazine and the slide magazine are connectable to one another via at least one first mechanical connection that encompasses at least one first mechanical connecting element of the slide magazine and at least one second mechanical connecting element, complementary to the first mechanical connecting element, of the cassette magazine. It is thereby possible to eliminate an additional component, thereby simplifying handling of the magazines.

It is particularly advantageous that the cassette magazine and the slide magazine are connectable to one another, in addition to the first mechanical connection, via a second mechanical connection that encompasses at least one third mechanical connecting element of the slide magazine and at least one fourth mechanical connecting element, complementary to the third mechanical connecting element, of the cassette magazine. The connecting elements for producing the first mechanical connection and the connecting elements for producing the second mechanical connection between the cassette magazine and the slide magazine are preferably arranged at the oppositely located ends of the cassette magazine and slide magazine, respectively. The second mechanical connection results in more secure retention between the cassette magazine and the slide magazine. It is thereby possible, especially when the apparatus is being transported, to prevent damage to the cassettes and the sample blocks arranged in the cassettes, and to the specimen slides.

The first mechanical connection is preferably a snap-lock connection. When the snap-lock connection is suitably embodied, a snap-lock connection of this kind can be easily opened or closed manually by operating personnel.

In addition, it is advantageous to allocate uniquely, to each specimen slide receiving region provided in the slide magazine for the reception of at least one specimen slide, a cassette receiving region provided in the cassette magazine for the reception of at least one cassette. This makes possible a unique allocation of the specimen slides arranged in the specimen slide receiving regions of the specimen slide receiving magazine, and the cassettes arranged in the cassette receiving regions of the cassette magazine, thereby preventing any confusion of specimen slides and thus possible incorrect allocation of a sample to a specimen slide.

It is particularly advantageous to arrange the specimen slide receiving regions in the slide magazine in such a way that with the slide magazine and cassette magazine in the connected state, each specimen slide receiving region is arranged directly next to that cassette receiving region to which it is allocated. The risk of incorrect allocation of a sample to a specimen slide can thereby be further reduced.

It is additionally advantageous to equip each cassette allocated to a cassette receiving region, and each specimen slide allocated to a specimen slide receiving region, with identifiers allocatable to one another. This enables simple allocation of cassettes and specimen slides.

It is particularly advantageous if the identifier of a cassette allocated to a cassette receiving region, and the identifier of the specimen slides that are allocated to a specimen slide receiving region allocated to the cassette receiving region, are identical. It thereby becomes particularly easy to allocate the specimen slides to a cassette.

It is furthermore advantageous if the cassette magazine encompasses a first coding element, and the slide magazine encompasses a second coding element. The slide magazine and the cassette magazine are uniquely identifiable with the aid of these coding elements. In addition, a cassette magazine and a slide magazine can be uniquely allocatable to one another with the aid of the coding elements. If multiple cassette magazines and slide magazines are being used simultaneously, this prevents an incorrect slide magazine from being allocated to a cassette magazine, or an incorrect cassette magazine from being allocated to a slide magazine.

The coding elements preferably encompass at least one information medium having at least one machine-readable coded datum. Electrical components, in particular transponders or RFID tags, are preferably used as information media.

The sample block to be processed preferably encompasses a biological sample embedded in hardened paraffin.

It is additionally advantageous to equip all the specimen slide receiving regions that are allocated to a first cassette receiving region with a respective color identifier of a first color, and to equip those specimen slide receiving regions that are allocated to a cassette receiving region that is arranged in the cassette magazine adjacently to the first cassette receiving region with a respective color identifier of a second color that is different, and by preference clearly distinguishable, from the first color. The risk of confusing specimen slides in the context of manual handling of the specimen slides can thereby be reduced.

In an advantageous embodiment of the invention, the apparatus is inserted into a microtome. For this, the apparatus and the microtome are configured in such a way that the apparatus, with both magazines, is deliverable to the microtome. The microtome preferably encompasses at least one first component for removal of a cassette, having the sample block to be processed, from a cassette receiving region of the cassette magazine. In addition, the microtome produces at least one thin section from the sample block contained in the removed cassette. The microtome furthermore encompasses a second component for removing a specimen slide allocated to the removed cassettes.

It is advantageous to embody the microtome and the apparatus in such a way that the slide magazine and the cassette magazine are deliverable to the microtome in the connected state. This substantially simplifies handling. Alternatively, the slide magazine and the cassette magazine can also be delivered separately to the microtome.

A further aspect of the invention relates to a method for handling multiple cassettes that each have at least one sample block having a sample to be processed, and multiple specimen slides. The cassettes each having a first identifier datum. In addition, each cassette has at least one specimen slide allocated to it, each specimen slide being identified with the first identifier datum of the cassette to which the specimen slide is allocated, or with a second identifier datum that can be allocated to the first identifier datum. Each cassette is allocated to one respective cassette receiving region of a cassette magazine. Likewise, each specimen slide is arranged in one respective specimen slide receiving region of the slide magazine. In addition, the slide magazine and the cassette magazine are connected to one another.

The method specified by the independent method claim can be further developed in the same manner as the apparatuses according to claim 1. In particular, the method can be further developed with the features described in the dependent claims that refer back to the apparatus, and in corresponding method features.

Further features and advantages of the invention are evident from the description that follows, which further explains the invention on the basis of exemplifying embodiments in combination with the appended Figures.

DETAILED DESCRIPTION OF THE DRAWINGS

Figure 1:
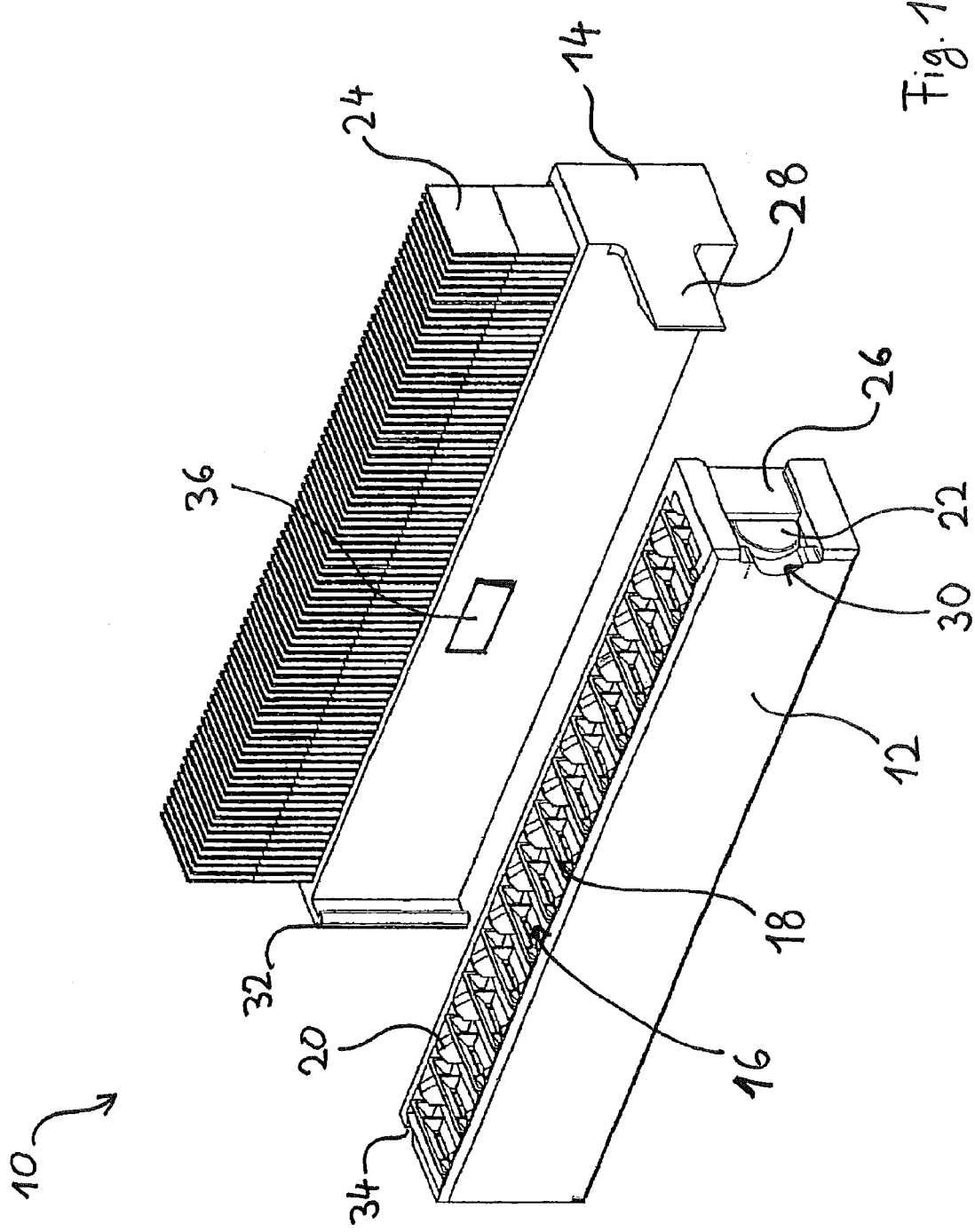
FIG. 1 is a schematic perspective depiction of an apparatus having a cassette magazine and a slide magazine, in the non-connected state.

FIG. 1 shows an apparatus 10 having a cassette magazine 12 and a slide magazine 14 in the non-connected state. The non-connected state is characterized by the fact that cassette magazine 12 and slide magazine 14 are not connected to one another.

Cassette magazine 12 has a plurality of cassette receiving regions. One cassette receiving region is designated, by way of example, with the reference character 16. The cassette receiving regions are also referred to as "compartments." Each cassette receiving region 16 is delimited by at least two guidance elements and by the side walls of cassette magazine 12. One guidance element is designated, by way of example, with the reference character 20. At least one cassette 18 can be received in each cassette receiving region 16. Cassette receiving regions 16 are preferably dimensioned in such a way that exactly one cassette 18 is introducible into each cassette receiving region 16.

One sample block 22 is arranged in each of cassettes 18. Sample block 22 encompasses a preferably biological sample that is embedded in an embedding material. By preference, the biological sample is embedded in paraffin.

Slide magazine 14 has a plurality of specimen slide receiving regions 25. At least one specimen slide 24 is arrangeable in each specimen slide receiving region 25. By preference, the specimen slide receiving regions 25 are configured in such a way that exactly one specimen slide 24 can be received in each specimen slide receiving region 25. Cassette receiving regions 16 of cassette magazine 12, and the specimen slide receiving regions 25 of slide magazine 14, are arranged in such a way that when cassette magazine 12 and slide magazine 14 are connected to one another, cassette receiving regions 16 and the specimen slide receiving regions 25 are arranged next to one another.

Cassette magazine 12 and slide magazine 14 are connectable to one another via two mechanical connections. The first mechanical connection is constituted by a first mechanical connecting element 28 of slide magazine 14, and a second mechanical connecting element 26 of cassette magazine 12. Second mechanical connecting element 26 is embodied in complementary fashion to first connecting element 28. The first mechanical connection is by preference a snap-lock connection. First mechanical connecting element 28 of slide magazine 14 is a resilient plate that is arranged on the side of slide magazine 14 facing toward cassette magazine 12, at a first end of slide magazine 14, and projects laterally therefrom. Second mechanical connecting element 26 of cassette magazine 12 is a cutout or engagement opening which is arranged in such a way that in the connected state, first mechanical connecting element 28 of slide magazine engages exactly into said cutout. First mechanical connecting element 28 has, on the side that faces cassette magazine 12 in the connected state, a protruding engagement element that, in the connected state, snap-locks into the cutout of second mechanical connecting element 26 of cassette magazine 12. The side wall of cassette magazine 12 facing away from slide magazine 14 comprises, at the end at which second mechanical connecting element 26 is arranged, a cutout 30 by means of which the first mechanical connection can be more easily released manually by pushing the resilient plate of first mechanical connecting element 28 away from cassette element 12.

Apparatus 10 further has a second mechanical connection. The second mechanical connection is constituted by a third mechanical connecting element 32 of slide magazine 14 and by a fourth mechanical connecting element 34, complementary to third mechanical connecting element 32, of cassette magazine 12. Mechanical connecting elements 32, 34 of the second mechanical connection are arranged on a second end of apparatus 10 opposite the first end of apparatus 10. In the present exemplifying embodiment, the third mechanical connecting element of slide magazine 14 is embodied as a spring that engages into a groove-shaped fourth mechanical connecting element 34 of cassette magazine 12.

Slide magazine 14 and cassette magazine 12 can be fixedly connected to one another by means of the mechanical connections, so that cassette magazine 12 and slide magazine 14 can be transported together. In particular, cassette magazine 12 and slide magazine 14 can, in this fashion, be delivered to a microtome workstation and, individually or together, to a microtome.

Cassette magazine 12 further encompasses a first coding element 37, and slide magazine 14 encompasses a second coding element 36. With the aid of coding elements 36 and 37, both slide magazine 14 and cassette magazine 12 are uniquely identifiable. In addition, with the aid of coding elements 37 and 36 a cassette magazine 12 and a slide magazine 14 are uniquely allocatable to one another. Coding elements 37 and 36 are preferably information media having at least one machine-readable, coded datum. The information media are preferably electrical components, in particular transponders or RFID tags.

Alternatively, coding elements 37 and 36 can also be mechanical coding elements. For example, the second coding element 36 of slide magazine 14 can encompass multiple pins arranged in a predefined pattern, and the first coding element 37 of cassette magazine 12 can encompass multiple recesses arranged in a specific pattern. Only if the pattern of the pins of second coding element 36 of slide magazine 14, and the pattern of the cutouts of the first coding element 37 of cassette magazine 12, correspond, can the slide magazine 14 and the cassette magazine 12 be connected to one another.

Cassettes 18 that are introducible into cassette magazine 12 each have an identifier 19 having information about sample block 22 contained in the respective cassette 18. This information encompasses, in particular, data with which it is possible to ascertain a patient from whom the sample embedded in sample block 22 was taken. In a microtome to which cassette magazine 12 and slide magazine 14 are deliverable, cassette 18 having sample block 22 contained therein is removed from cassette magazine 12. With the aid of a sectioning apparatus of the microtome, at least one thin section is produced from sample block 22 for subsequent microscopic investigation. The thin section is mounted onto a specimen slide 24, then covered with a coverslipping agent and a coverslip, and delivered to at least one further apparatus for further investigation, in particular for microscopic investigation. Each specimen slide 24 also comprises an specimen slide identifier 35. The specimen slide identifier 35 of specimen slide 24 must be capable of being allocated unequivocally to the cassette identifier 19 of cassette 18 that contains sample block 22 from which the thin section mounted on the specimen slide was produced. By preference, the cassette identifier 19 of cassette 18 and the specimen slide identifier 35 of specimen slide 24 to be allocated are identical. In the exemplifying embodiment, specimen slides 24 are already identified before they are received in the specimen slide receiving regions 25 of slide magazine 14. In this fashion, only one specimen slide labeling device is required, and fully automatic or semi-automatic handling of specimen slides 24 becomes possible.

Multiple specimen slide receiving regions 25 of slide magazine 14 are allocated to each cassette receiving region 16 of cassette magazine 12. This avoids confusion about the allocation of specimen slides 24 to the respective cassettes 18. Preferably, a specific number of specimen slide receiving regions 25 are predefined in each cassette receiving region 16 of cassette magazine 12, and the same number of specimen slide receiving regions 25 is allocated to each cassette receiving region 16. If fewer specimen slide receiving regions 25 are needed than are provided for a cassette receiving region 16, the corresponding specimen slide receiving regions 25 then remain empty. Allocation of cassettes 18 into cassette receiving regions 16 of cassette magazine 12, and allocation of specimen slides 24 into specimen slide receiving regions 25 of slide magazine 14, can be accomplished automatically by way of a sorting machine. Both cassette magazine 12 and slide magazine 14 are embodied so that they are suitable for automatic loading with cassettes 18 and with specimen slides 24, respectively, and are likewise suitable for automatic delivery of cassettes 18 and specimen slides 24 to the microtome.

As a result of the coding of cassette magazine 12 and of slide magazine 14, and as a result of the unique allocation of cassette receiving regions 16 and the specimen slide receiving regions 25, a unique allocation of an cassette identifier of a cassette 18 to a specific cassette receiving region 16 in a specific cassette magazine 12 can occur in a database. In addition, the exact specimen slide receiving regions 25 of the specimen slides 24 belonging to a cassette 18 in a specific specimen slide magazine 14 can be gathered from the database. This allows the processing status to be monitored externally at any time.

The specimen slide receiving regions 25 are preferably arranged in slide magazine 14 in such a way that when slide magazine 14 and the cassette magazine 12 are connected to one another, each specimen slide receiving region 25 is arranged directly next to that cassette receiving region 16 to which it is allocated.

In addition, all the specimen slide receiving regions 25 that are allocated to a first cassette receiving region 16 can each have a first color identifier 38 of a first color, and those specimen slide receiving regions 25 that are allocated to a second cassette receiving region 16 that is arranged in cassette magazine 12 adjacently to first cassette receiving region 16 can each have a second color identifier 39 of a second color that is different, and by preference clearly distinguishable, from the first color. The probability of error in the context of manual allocation of specimen slides 24 to a specimen slide receiving region 25, and of cassette magazine 12 to a cassette receiving region 16, is thereby reduced.

Apparatus 10, and the microtome to which apparatus 10 is to be delivered, are preferably embodied in such a way that slide magazine 14 and cassette magazine 12 are deliverable to the microtome in the connected state.

Figure 2:
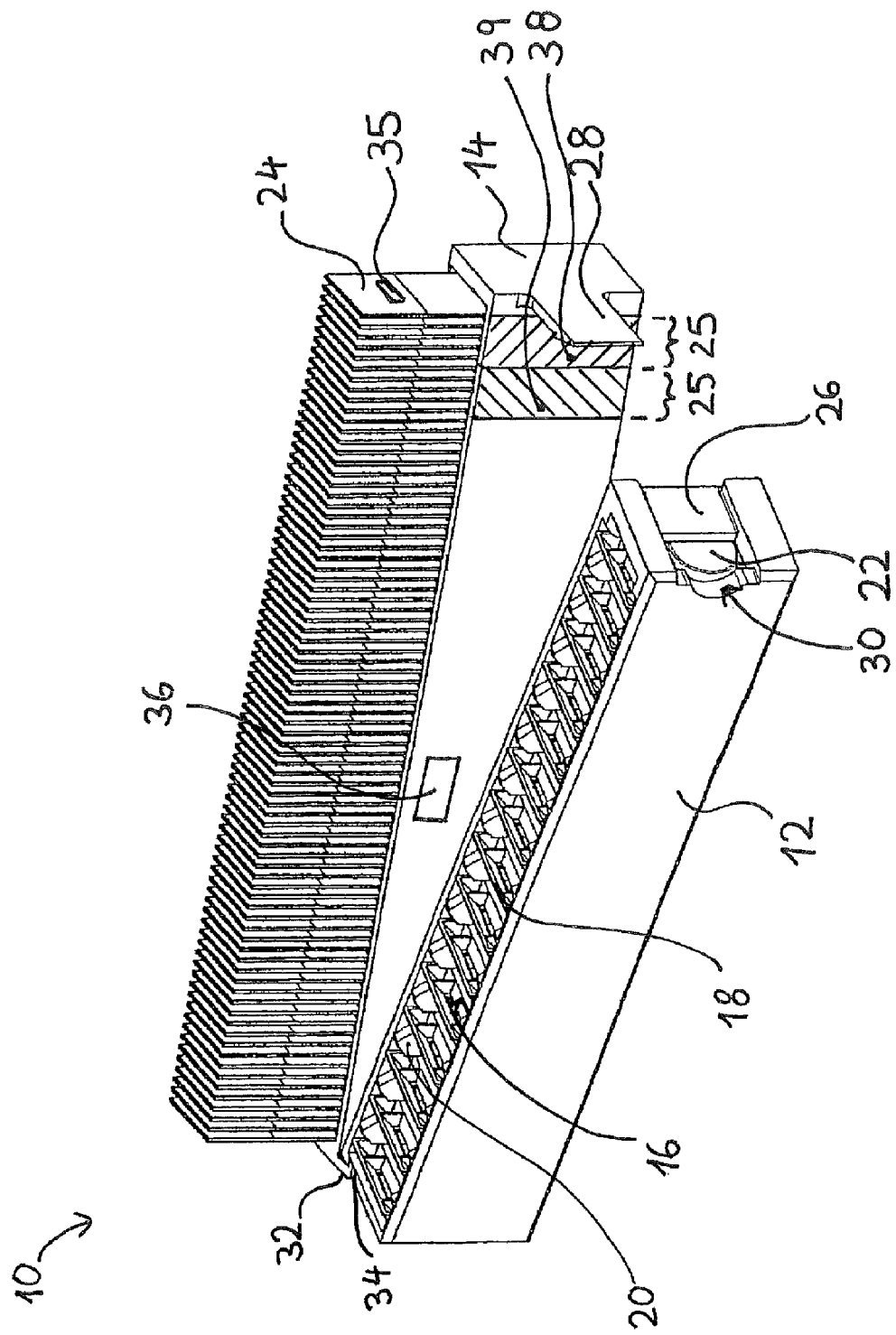
FIG. 2 is a schematic perspective depiction of the apparatus according to FIG. 1 in a position as the cassette magazine and slide magazine are being brought together.

FIG. 2 is a schematic perspective depiction of apparatus 10 of FIG. 1 in a position as the cassette magazine and slide magazine are being brought together. Elements having the same configuration or the same function have the same reference characters. The spring-shaped third connecting element 32 of slide magazine 14 engages into the groove-shaped fourth connecting element of cassette magazine 12. In the position shown in FIG. 2, first mechanical connecting element 28 of slide magazine 14 and second mechanical connecting element 26 of cassette magazine 12 are not yet connected to one another.

Figure 3:
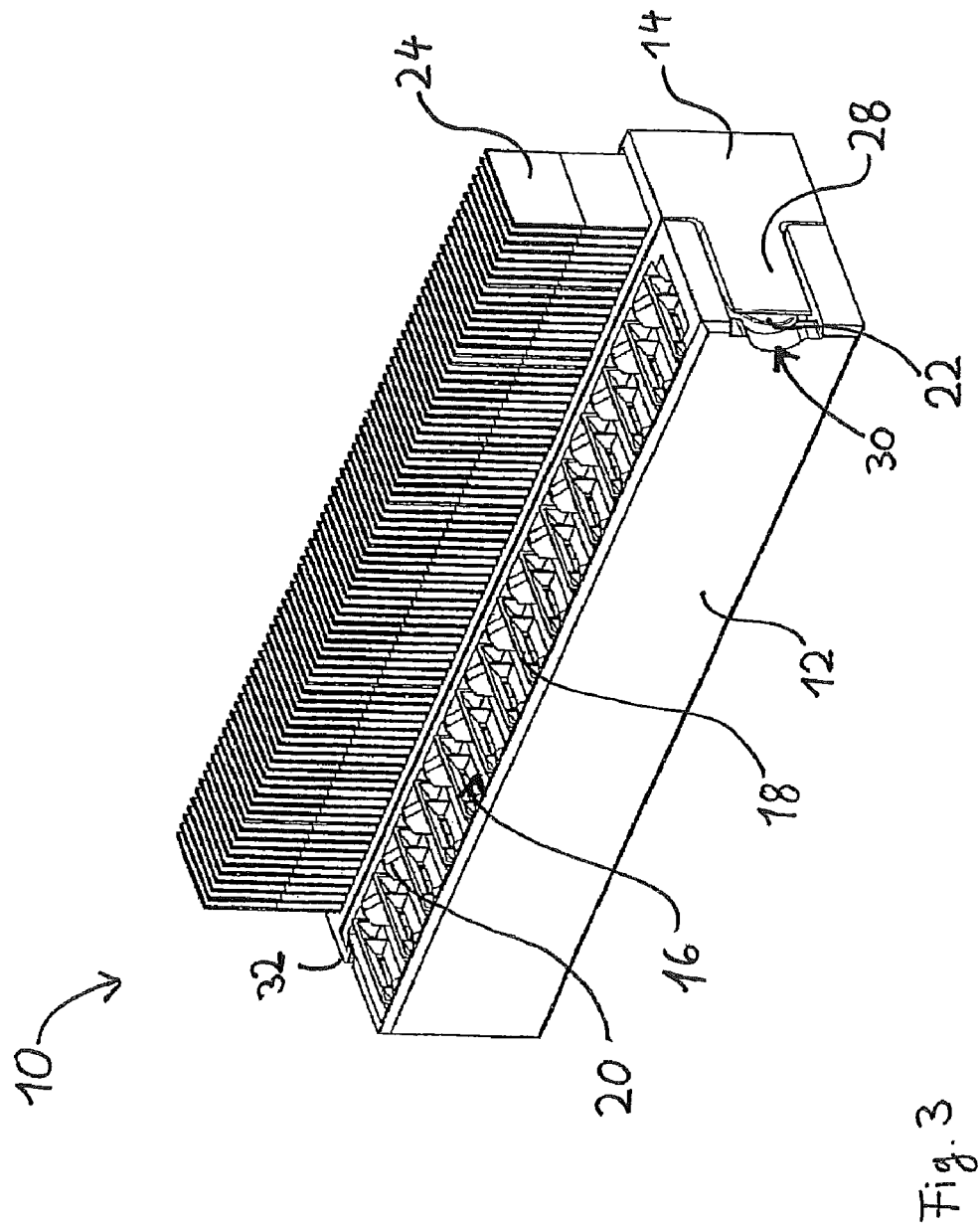
FIG. 3 is a schematic perspective depiction of the apparatus according to FIGS. 1 and 2 in the connected state.

FIG. 3 is a further schematic perspective depiction of apparatus 10 according to FIGS. 1 and 2. In FIG. 3, cassette magazine 12 and slide magazine 14 are connected to one another by way of both the first mechanical connection and the second mechanical connection.

Figure 4:
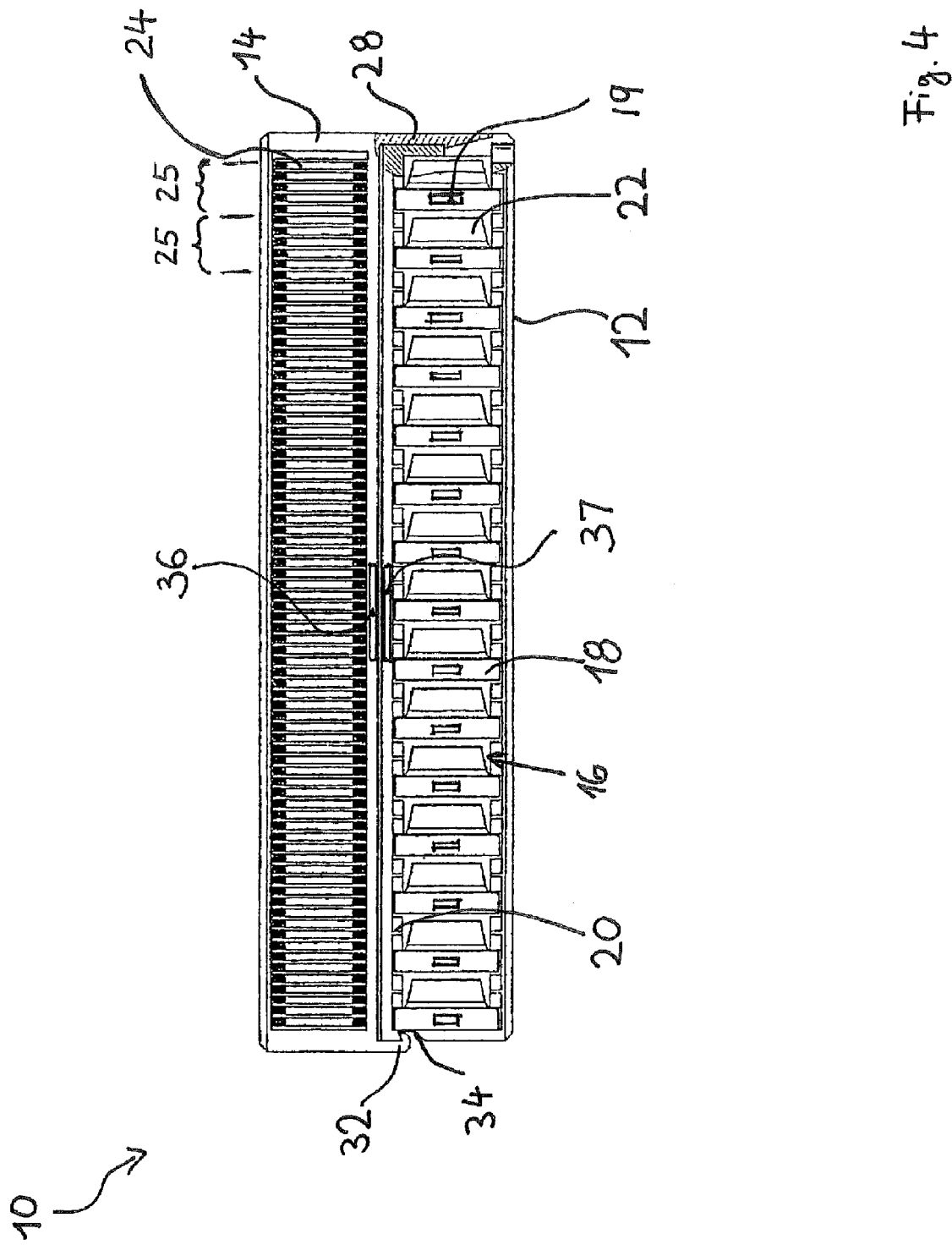
FIG. 4 is a plan view of a schematic, partly sectioned depiction of the apparatus according to FIGS. 1 to 3.

FIG. 4 is a plan view of a schematic, partly sectioned depiction of apparatus 10 according to FIGS. 1 to 3. Cassette magazine 12 and slide magazine 14 are connected to one another. At the end of slide magazine 14 and of cassette magazine 12 at which the first mechanical connection is arranged, slide magazine 14 and cassette 12 are depicted in section to the extent that first connecting element 28 and second connecting element 26 are at least partly visible.

Slide magazine 14 and cassette magazine 12 can alternatively be connected to one another via catch closures or via slightly conical insertion closures, or other suitable connecting elements. Connecting elements 26, 28, 32, 34 can furthermore be magnets.

LIST OF REFERENCE NUMERALS

10 Apparatus
12 Cassette magazine
14 Slide magazine
16 Cassette receiving region
18 Cassette
19 Cassette identifier
20 Guidance element
22 Sample block
24 Specimen slide
25 Specimen slide receiving region
26, 28, 32, 34 Connecting element
35 Specimen slide identifier
30 Cutout
36 First coding element
37 Second coding element
38 First color identifier
39 Second color identifier

What is claimed is:

1. An apparatus for storing at least one specimen slide and at least one cassette comprising a sample that is embedded in a sample block and that is to be processed, said apparatus comprising:

a cassette magazine adapted to receive a plurality of cassettes in respective cassette receiving regions, said cassettes having at least one sample block;

a slide magazine adapted to receive a plurality of specimen slides in respective specimen slide receiving regions; and at least one connecting element for connecting the cassette magazine and the slide magazine mechanically with each other; wherein the respective cassette receiving regions are allocated in a predefined manner to respective specimen slide receiving regions such that when the slide magazine and cassette magazine are connected to one another each specimen slide receiving region is arranged directly next to that cassette receiving region to which it is allocated.

2. The apparatus according to claim 1, further comprising:
at least one first mechanical connection that comprises:
   at least one first mechanical connecting element of the slide magazine; and
   at least one second mechanical connecting element that is complementary to the first mechanical connecting element of the cassette magazine; wherein
the cassette magazine and the slide magazine are connectable to one another by engaging the first and second mechanical connecting elements with each other.

3. The apparatus according to claim 2, further comprising:
a second mechanical connection that comprises:
   at least one third mechanical connecting element of the slide magazine; and
   at least one fourth mechanical connecting element that is complementary to the third mechanical connecting element of the cassette magazine; wherein
the cassette magazine and the slide magazine are connectable to one another by engaging the third and fourth mechanical connecting elements with each other.

4. The apparatus according to claim 3, wherein
the first and second connecting elements are arranged at a first end of the cassette magazine and slide magazine;
the third and second connecting elements are arranged at a second end of the cassette magazine and slide magazine that is located opposite of the first end of the cassette magazine and slide magazine; and
the cassette magazine and the slide magazine are connectable to one another by engagement of the first with the second mechanical elements and the third with the fourth mechanical elements.

5. The apparatus according to claim 2, wherein the first mechanical connection is a snap-lock connection.

6. The apparatus according to claim 1, wherein each cassette allocated to a cassette receiving region has a cassette identifier, and each specimen slide allocated to a specimen slide receiving region has a specimen slide identifier, and the cassette identifier and the specimen slide identifier are allocatable to one another.

7. The apparatus according to claim 6, wherein the cassette identifier and the specimen slide identifier.

8. The apparatus according to claim 1, wherein the cassette magazine comprises a first coding element, the slide magazine comprises a second coding element, the slide magazine and the cassette magazine are clearly identifiable by the first and second coding elements, and a cassette magazine and a slide magazine are allocatable in a predefined manner to one another by the aid of the first and second coding elements.

9. The apparatus according to claim 8, wherein the first and second coding elements comprise at least one information medium having at least one machine-readable coded information.

10. The apparatus according to claim 1, wherein the sample block comprises a biological sample embedded in hardened paraffin.

11. The apparatus according to claim 1, wherein all the specimen slide receiving regions that are allocated to a first cassette receiving region have a respective first color identifier of a first color; and those specimen slide receiving regions that are allocated to a second cassette receiving region that is arranged in the cassette magazine adjacent to the first cassette receiving region each have a second color identifier of a second color that is different and clearly distinguishable from the first color.

12. A method for handling multiple cassettes that each have at least one sample block having a sample to be processed, and for handling multiple specimen slides, said method comprising:
   providing each of the cassettes with a first identification tag;
   allocating at least one specimen slide to each cassette;
   identifying each specimen slide by the first identification tag of the cassette to which the respective specimen slide is allocated, or by a second identification tag that can be allocated to the first identification tag;
   arranging each cassette in one respective cassette receiving region of a cassette magazine;
   arranging each specimen slide in one respective specimen slide receiving region of a slide magazine; and
   connecting the slide magazine and the cassette magazine to one another so that when connected each specimen slide is arranged directly next to that cassette to which it is allocated.

* * * * *

UNITED STATES PATENT AND TRADEMARK OFFICE
CERTIFICATE OF CORRECTION

PATENT NO. : 8,192,136 B2
APPLICATION NO. : 12/567440
DATED : June 5, 2012
INVENTOR(S) : Roland Walter et al.

Page 1 of 1

It is certified that error appears in the above-identified patent and that said Letters Patent is hereby corrected as shown below:

Claim 7 currently reads:

The apparatus according to claim 6, wherein the cassette identifier and the specimen slide identifier.

Claim 7 should read:

The apparatus according to claim 6, wherein the cassette identifier and the specimen slide identifier are identical.

Signed and Sealed this
Twenty-sixth Day of March, 2013

Teresa Stanek Rea
*Acting Director of the United States Patent and Trademark Office*